US00PP18805P2

(12) United States Plant Patent
O'Byrne

(10) Patent No.: US PP18,805 P2
(45) Date of Patent: May 13, 2008

(54) ***AJUGA* PLANT NAMED 'TOFFEE CHIP'**

(50) Latin Name: *Ajuga reptans*
Varietal Denomination: Toffee Chip

(76) Inventor: Marietta O'Byrne, 86813 Central Rd., Eugene, OR (US) 97402

( * ) Notice: Subject to any disclaimer, the term of this patent is extended or adjusted under 35 U.S.C. 154(b) by 0 days.

(21) Appl. No.: 11/527,639

(22) Filed: Sep. 25, 2006

(51) Int. Cl.
*A01H 5/00* (2006.01)

(52) U.S. Cl. ..... Plt./373
(58) Field of Classification Search ..... Plt./263, Plt./373
See application file for complete search history.

(56) References Cited

U.S. PATENT DOCUMENTS

PP15,815 P2 * 6/2005 Tristram ..... Plt./373

* cited by examiner

*Primary Examiner*—Wendy Haas
(74) *Attorney, Agent, or Firm*—Klarquist Sparkman, LLP

(57) ABSTRACT

A new and distinct form of *Ajuga reptans* plant characterized by its unique foliage coloration and markings. Mature leaves are colored gold to cream on the margin with shades of gray green in the center. New leaves show brown and khaki shades. It has a dwarf habit, small, narrow leaves, and blue flowers on ten centimeter spikes.

1 Drawing Sheet

Botanical Denomination: *Ajuga reptans.*
Variety Designation: 'Toffee Chip'.

BACKGROUND OF THE INVENTION

The present invention relates to a new and distinct cultivar of *Ajuga reptans,* given the name, 'Toffee Chip'. *Ajuga* is in the family Lamiaceae. This plant originated from a naturally occurring meristematic mutation of *Ajuga* 'Chocolate Chip' (an unpatented plant with the synonym 'Valfredda'). The mutated plant was found in a garden at an Oregon nursery.

This plant is unique in its foliage coloration and markings. Mature leaves are colored gold to cream on the margin with shades of gray green in the center. New leaves show brown and khaki shades. 'Toffee Chip' has the same great attributes of its parent, the dwarf habit, the small, narrow leaves and blue flowers on ten centimeter spikes.

The new variety has been reproduced only by asexual propagation (division and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old *Ajuga* 'Toffee Chip' growing in the garden in fall in Canby, Oreg.

DETAILED PLANT DESCRIPTION

The following is a detailed description of the new *Ajuga* cultivar based on observations of two-year-old specimen grown outside in the ground in the garden in Canby, Oreg.

The color descriptions are all based on The Royal Horticultural Society Colour Chart.

Plant:
- *Form.*—Stoloniferous, herbaceous perennial.
- *Cold hardiness.*—USDA Zone 4–9.
- *Size.*—Grow to 23 cm wide and 5 cm high.
- *Vigor.*—Good.
- *Stem.*—Rosette.
- *Roots.*—White 155B, thickened to fibrous, plants root easily from divisions.
- *Stolons.*—White 155B, 1.5 mm wide, internodes grow to 14 mm long.

Leaf:
- *Type.*—Simple.
- *Arrangement.*—Opposite in a basal rosette.
- *Shape.*—Spatulate.
- *Venation.*—Pinnate.
- *Margins.*—Entire.
- *Apex.*—Obtuse.
- *Base.*—Attenuate.
- *Blade size.*—Grows to 3.4 cm long and 1 cm wide.
- *Surface texture.*—Very sparsely pubescent on both sides.
- *Petiole description.*—1 cm long and 2 mm wide, very sparsely pubescent, Yellow Green 146D with maroon tinted base, Greyed Red 178A.
- *Leaf color.*—Top side — very young leaves — Greyed Green 197A overall, giving the toffee color. — mature leaves — outer margin is Greyed Yellow 160B with the center two tones of grey green, Greyed Green 191A and 191C. — older leaves — outer margin is Yellow White 158A with the center two tones of grey green, Greyed Green 191A and 191C. Bottom side — same.

Inflorescence:
- *Type.*—Terminal spike.
- *Number of flowers.*—70 per spike in two to five flowered, dense whorls.

*Peduncle.*—9.5 cm tall and 2.3 mm wide, pubescent, Grey Green 191A with tints of Greyed Orange 197A.

*Pedicel.*—None, flowers sessile.

*Floral leaves.*—Subtending flowers, sessile, ovate to broadly elliptic, size changes from bottom leaf 1.3 cm wide and 1.6 cm long to top floral leaves 6 mm long and 2.5 mm wide, color same as older leaves above.

*Bloom period.*—April to June in Canby, Oreg.

Flower bud:

*Size.*—7 mm long and 2 mm wide at the widest point prior to opening.

*Description.*—Tubular.

*Surface texture.*—Villous.

*Color.*—Closest to Violet Blue 97A.

Flower:

*Type.*—Zygomorphic.

*Shape.*—Bilabiate.

*Corolla description.*—1 cm long and spreads to 4.5 mm wide, tube and throat 5 mm long and 1 mm to 1.5 mm wide, 2 small upper lobes less than 1 mm long and wide, acute, three lower lobes, two spreading sideways, the terminal lobe two lobed and obovate, entire, glabrous inside, villous outside, color inside Violet Blue 94B, outside Violet Blue 91A.

*Calyx description.*—5 lobed, acute, entire, pubescent outside, glabrous inside.

*Pistil description.*—9 mm long, ovary 0.5 mm long, Yellow Green 146C, style and stigma 8.5 mm long, Violet Blue 92 A at the tip to 92D at the base.

*Stamen description.*—4.

*Fragrance.*—None.

*Lastingness.*—A spike blooms for about 3 weeks on the plant.

Fruit: None, plant sterile.

Seed: None, plant sterile.

Pests and diseases: *Ajuga* are known to be susceptible to southern blight and various fungal leaf spots, crown rot, and fungal root rot. The new cultivar has shown good mildew resistance in Canby, Oreg.

Comparisons: Compared to *Ajuga reptans* 'Chocolate Chip' which is described in the Terra Nova Nurseries 2003 catalog as a "curious, spreading miniature, chocolate foliage shining with lacy blue flowers to 3 inches tall," *Ajuga* 'Toffer Chip' has light gold leaf margins and a mottled gray green center. It is not as shiny.

I claim:

1. A new and distinct form of *Ajuga* plant substantially as shown and described.

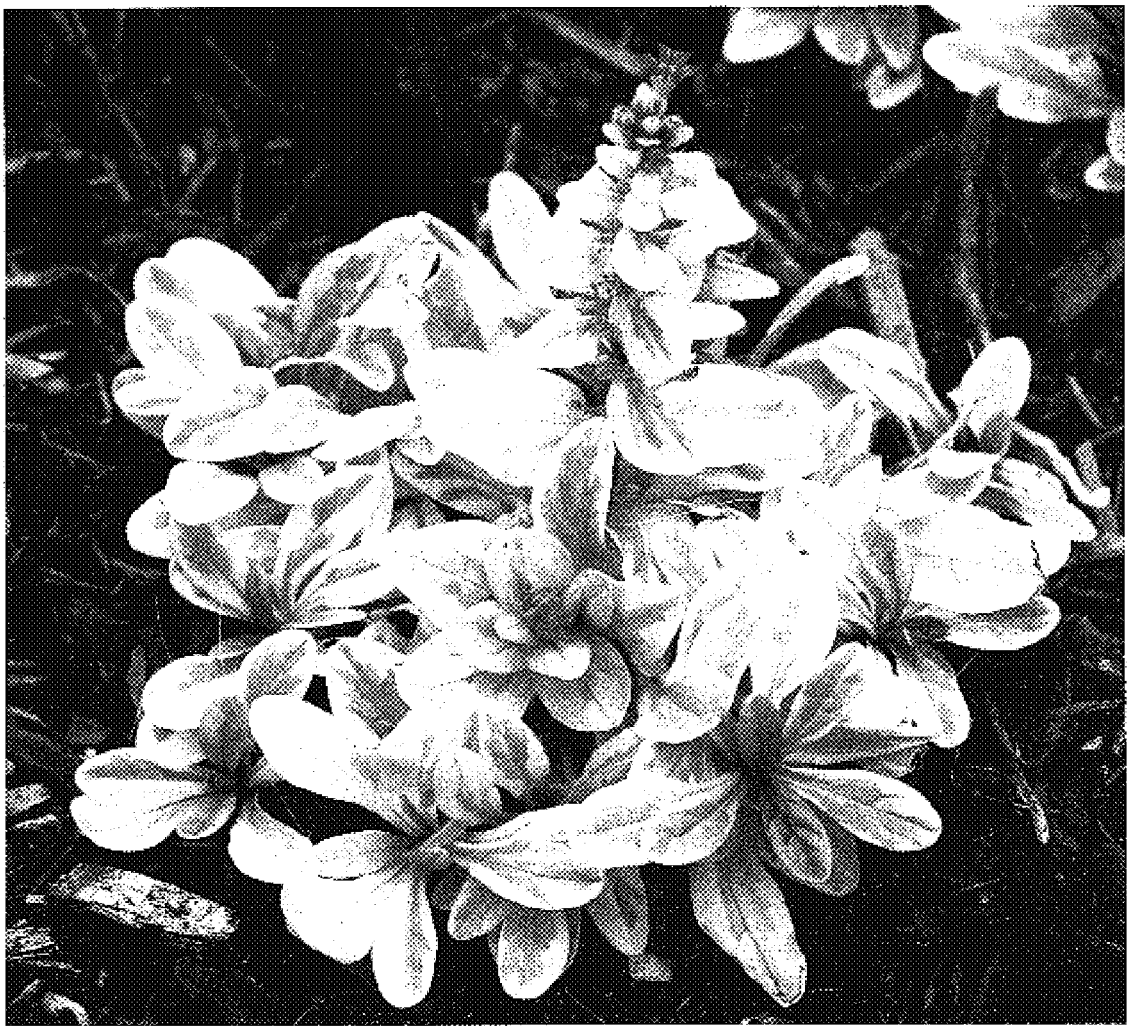

* * * * *